US012806127B2

(12) United States Patent
Simonet et al.

(10) Patent No.: US 12,806,127 B2
(45) Date of Patent: Nov. 24, 2026

(54) EMULSIONS CONTAINING BIS-ETHYLHEXYLOXYPHENOL METHOXYPHENYL TRIAZINE, LIPOPHILIC ACRYLIC POLYMER, FATTY ACID ESTER AND ANIONIC SURFACTANT

(71) Applicant: L'OREAL, Paris (FR)

(72) Inventors: Frédéric Simonet, Clichy (FR); Juliette Beiller, Chevilly-Larue (FR); Widad Ajili, Chevilly-Larue (FR)

(73) Assignee: L'OREAL, Paris (FR)

( * ) Notice: Subject to any disclaimer, the term of this patent is extended or adjusted under 35 U.S.C. 154(b) by 405 days.

(21) Appl. No.: 18/543,823

(22) Filed: Dec. 18, 2023

(65) Prior Publication Data

US 2025/0195375 A1 Jun. 19, 2025

(51) Int. Cl.

| | |
|---|---|
| ***A61K 8/49*** | (2006.01) |
| ***A61K 8/06*** | (2006.01) |
| ***A61K 8/81*** | (2006.01) |
| ***A61Q 19/00*** | (2006.01) |

(52) U.S. Cl.

CPC .............. *A61K 8/4966* (2013.01); *A61K 8/06* (2013.01); *A61K 8/8152* (2013.01); *A61Q 19/00* (2013.01); *A61K 2800/10* (2013.01); *A61K 2800/30* (2013.01)

(58) Field of Classification Search

None

See application file for complete search history.

(56) References Cited

U.S. PATENT DOCUMENTS 11,510,860 B2 * 11/2022 Douezan .............. A61K 8/8152

FOREIGN PATENT DOCUMENTS

| | | | |
|---|---|---|---|
| FR | 3134516 | A1 | 10/2023 |
| WO | 2019/096956 | A1 | 5/2019 |
| WO | 2023/198923 | A1 | 10/2023 |

OTHER PUBLICATIONS

Mintel, "Tinted Fluid SPF 50+," Record ID: 9450630, Mar. 2022, XP093275993, 8 pp.

International Search Report and Written Opinion issued May 23, 2025, in International Application No. PCT/IB2024/000728.

* cited by examiner

*Primary Examiner* — Brian J Davis

(74) *Attorney, Agent, or Firm* — Womble Bond Dickinson (US) LLP

(57) ABSTRACT

The present disclosure relates to compositions including 2,4-bis-{[4-(2-ethyl hexyloxy)-2-hydroxy]-phenyl}-6-(4-methoxyphenyl)-1,3,5-triazine at least one lipophilic acrylic polymer, at least one $C_{12}$-$C_{24}$ fatty acid ester of a $C_2$-$C_{24}$ polyol, and at least one carboxylic or carboxylate anionic surfactant selected from the group consisting of amino acids modified with at least one $C_8$-$C_{30}$ hydrocarbon-based chain and salts thereof, as well as to methods of making and using such compositions.

16 Claims, No Drawings

EMULSIONS CONTAINING BIS-ETHYLHEXYLOXYPHENOL METHOXYPHENYL TRIAZINE, LIPOPHILIC ACRYLIC POLYMER, FATTY ACID ESTER AND ANIONIC SURFACTANT

FIELD OF THE INVENTION

The present disclosure relates to oil-in-water (O/W) emulsion compositions (emulsions) comprising 2,4-bis-{[4-(2-ethyl hexyloxy)-2-hydroxy]-phenyl}-6-(4-methoxyphenyl)-1,3,5-triazine (INCI name: bis-ethylhexyloxyphenol methoxyphenyl triazine), at least one lipophilic acrylic polymer, at least one $C_{12}$-$C_{24}$ fatty acid ester of a $C_2$-$C_{24}$ polyol, and at least one carboxylic or carboxylate anionic surfactant selected from the group consisting of amino acids modified with at least one $C_8$-$C_{30}$ hydrocarbon-based chain and salts thereof, as well as to methods of making and using such compositions.

DISCUSSION OF BACKGROUND

Radiation of wavelengths between 290 nm and 400 nm allows tanning of the human epidermis, while radiation of wavelengths between 290 and 320 nm, called UVB rays, hinders the development of a natural tan. Exposure is also likely to lead to a detrimental change in the biomechanical properties of the epidermis, resulting in the appearance of wrinkles leading to premature aging of the skin (i.e. photoaging).

UVA rays with wavelengths between 320 and 400 nm penetrate deeper into the skin than UVB rays. UVA rays cause immediate and persistent browning of the skin. Daily exposure to UVA rays, even for a short time, under normal conditions can damage collagen fibers and elastin, resulting in a change in the microrelief of the skin, the appearance of wrinkles and uneven pigmentation (spots, lack of uniformity of complexion).

Many studies show the need for effective protection against UVA and UVB to prevent sunburn, photoaging, and the like.

In order to obtain a high protection product, it is generally necessary to combine a large number of sunscreens and/or a high amount of UV filters to achieve high levels of filtering efficiency. However, high levels of UV filters do not lend themselves to an easy elaboration of compositions with a stabilized and pleasant texture.

There remains a need in the art for improved consumer care compositions which possess organic UV filters and have pleasant application properties (e.g., non-greasy feeling) and UV protection properties.

Accordingly, one aspect of the present disclosure is a composition which possesses organic UV filters and has pleasant application properties (e.g., non-greasy feeling) and UV protection properties.

SUMMARY OF THE INVENTION

The present disclosure relates to emulsion compositions comprising bis-ethylhexyloxyphenol methoxyphenyl triazine (BEMT or bemotrizinol), at least one lipophilic acrylic polymer, at least one $C_{12}$-$C_{24}$ fatty acid ester of a $C_2$-$C_{24}$ polyol, and at least one carboxylic or carboxylate anionic surfactant selected from the group consisting of amino acids modified with at least one $C_8$-$C_{30}$ hydrocarbon-based chain and salts thereof. Preferably, the pH of the emulsion composition is 6 or higher.

The present disclosure also relates to methods of treating, caring for, protecting, enhancing the appearance of, and/or making up a keratinous material comprising applying compositions of the present disclosure to a keratinous material in an amount sufficient to treat, care for, enhance the appearance of, and/or make up the keratinous material.

The present disclosure also relates to methods of making emulsion compositions comprising combining bis-ethylhexyloxyphenol methoxyphenyl triazine, at least one lipophilic acrylic polymer, at least one $C_{12}$-$C_{24}$ fatty acid ester of a $C_2$-$C_{24}$ polyol, and at least one carboxylic or carboxylate anionic surfactant selected from the group consisting of amino acids modified with at least one $C_8$-$C_{30}$ hydrocarbon-based chain and salts thereof, during formation of the emulsions. Preferably, the pH of the emulsion composition is 6 or higher.

It is to be understood that both the foregoing general description and the following detailed description are exemplary and explanatory only, and are not restrictive of the disclosure.

DETAILED DESCRIPTION OF THE INVENTION

In the following description and the claims appended hereto, it is to be understood that the terms used have their ordinary and accustomed meanings in the art, unless otherwise specified.

"About" as used herein means within 10% of the indicated number (e.g., "about 10%" means 9%-11% and "about 2%" means 1.8%-2.2%).

"A" or "an" as used herein means "at least one."

"At least one" means one or more and thus includes individual components as well as mixtures/combinations.

As used herein, all ranges provided are meant to include every specific point and range within, and combination of subranges between, the given ranges. Thus, a range from 1-5 includes specifically the integers within the range 1, 2, 3, 4 and 5, as well as subranges such as and 2-5, 3-5, 2-3, 2-4, 1-4, etc., as well as all fractional numbers within the range such as 1.2, 2.3, 3.4, etc., and subranges including such fractional numbers such as 1.5-3.8, 2-4.3, 4.2-4.9, etc.

"Film former", "film-forming polymer" or "film-forming agent" as used herein means a polymer or resin which is capable of leaving a film on the substrate to which it is applied, for example, after a solvent accompanying the film former has evaporated, absorbed into and/or dissipated on the substrate.

"Substituted" as used herein, means comprising at least one substituent. Non-limiting examples of substituents include atoms, such as hydrogen atoms or chlorine atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 115° C.

"Non-volatile", as used herein, means having a flash point of greater than about 115° C.

"Polymer" as used herein means a compound which is made up of at least two monomers.

"Free" or "substantially free" or "devoid of" as it is used herein means that while it is preferred that no amount of the specific component be present in the composition, it is possible to have very small amounts of it in the compositions of the disclosure provided that these amounts do not materially affect at least one, preferably most, of the advantageous properties of the compositions of the disclosure. Thus, for example, "free of oil" means that an effective amount (that is, more than trace amounts) of oil(s) is/are omitted from the composition (that is, about 0% by weight), "substantially free of oil" means that oil(s) is/are present in amounts not greater than 0.1% by weight, and "devoid of oil" means that oil(s) is/are present in amounts not greater than 0.25% by weight, based on the total weight of the composition. The same nomenclature applies for all other ingredients identified throughout the application and in this paragraph such as, for example, specific UV filters and/or surfactants (compositions of the disclosure which are "free of oxybenzone and/or octinoxate," "substantially free of oxybenzone and/or octinoxate," and "devoid of oxybenzone and/or octinoxate," as well as "free of surfactants," "substantially free of surfactants," and "devoid of surfactants," have meanings consistent with the discussion within this paragraph), even if not specifically discussed for each identified ingredient in the application. Discussed examples of the use of such language such as those in this paragraph are intended to be exemplary, not limiting.

"UV filters" as it is used herein means sunscreen active agents approved by a governmental regulatory agency such as the Food and Drug Administration (FDA) in the U.S. or the EU Commission in Europe and includes organic UV filters such as avobenzone, octocrylene, benzophenones, benzotriazoles and merocyanines, as well as mineral UV filters such as zinc oxide (ZnO) and titanium dioxide (TiO2).

"Anhydrous" as it is used herein means that compositions of the disclosure contain less than 3% water, meaning that the compositions can also contain less than 2% water, and less than 1% water, as well as being "free of water," "substantially free of water," and "devoid of water" as defined above.

"Keratinous materials" means nails (finger and/or toe nails), skin such as body, face, and eye area, scalp, keratin fibers such as eyelashes, eyebrows, and hair, and mucous membranes such as lips.

"Physiologically acceptable" means compatible with keratinous materials and having a pleasant color, odor and feel, and which does not cause any unacceptable discomfort (stinging or tautness) liable to discourage a consumer from using the composition. Preferably, the pH of the emulsion composition is 6 or higher, preferably 6.5 or higher, and preferably 7 or higher.

"UV protection efficiency" or "filtering efficiency" in the context of the present disclosure, is evaluated from one or more of SPF, UVAPF, Critical Wavelength, and UVA-1/UV ratio.

"SPF" (Sun Protection Factor) measures the level of protection against erythema provided by a composition. The SPF value corresponds to the ratio between the minimum erythemal dosage (MED) measured wearing the composition and the MED measured with bare skin. "SPF" is a known term in the sunscreen art and is defined, for example, in A new substrate to measure sunscreen protection factors throughout the ultraviolet spectrum, J. Soc. Cosmet. Chem., 40, 127-133 (May/June 1989).

The evaluation of the SPF (Sun Protection Factor) can be performed, for example, in vitro with spectrophotometer by Labsphere (North Sutton, NH, USA). In such an evaluation, the plate is the material on which the tested composition is applied. For such an evaluation, polymethylmethacrylate (PMMA) plates can be used. An example of an acceptable protocol is in the process of ISO accreditation under the name ISO Committee Draft 23675.

The evaluation of the Sun Protection Factor (SPF) can also be performed in-vivo according to the ISO 24444:2019 protocol "Cosmetics-Sun protection test methods-In-vivo determination of the sun protection factor (SPF)." Also, it can be determined according to FDA protocols, as described in the document "Labeling and Effectiveness Testing; Sunscreen Drug Products for Over-the-Counter Human Use" published in the US Federal Register on Jul. 5, 2011 (https://www.federalregister.gov/d/2011-14766); 21 C.F.R. Part 352 Subpart D § 352.72, updated and revised by the 2011 publication in the Federal Register.

"UVAPF" (UVA protection factor) relates to an index characterizing the protection against UVA provided by a composition. For example, the UVAPF index can be measured in vivo according to the "PPD" (Persistent Pigment Darkening) method in the ISO-24442:2022 protocol, measuring observed skin color 2 to 4 hours after UVA exposure. Also, it can be determined according to FDA protocols, again as described in 21 C.F.R. Part 352 Subpart D § 352.72 as discussed above in connection with SPF.

The evaluation of UVA protection can also be measured in vitro with the Labsphere® spectrophotometer under conditions such as those discussed above in connection with SPF. ISO 24443:2021 protocol describes such an in vitro method.

FDA broad spectrum testing procedures, in particular "critical wavelength" testing procedures, can also be found at 21 C.F.R. Part 352 Subpart D § 352.72. Also, broad spectrum testing procedures include determining the UVA1/UV ratio as described in "Sunscreen Drug Products for Over-the-Counter Human Use" published in the Federal Register https://www.federalregister.gov/documents/2019/02/26/2019-03019/sunscreen-drug-products-for-over-the-counter-human-use." In the assay outlined in the monograph, known as the Boots adaptation of the Diffey/Robson test method, a ratio is generated of the protection afforded by the sunscreen product from UVA1 (340-400 nm) compared to the protection from total UV radiation (UVB and UVA at 290-400 nm) calculated from the absorbance curve. This ratio UVA1/UV would represent the score for the product in the in vitro test.

According to the present disclosure, compositions of the present disclosure preferably have one or more of the following properties:

- Compositions have a critical wavelength as determined by FDA's critical wavelength procedures of at least 370 nm;
- Compositions have an SPF value of at least 15, preferably at least 30, preferably at least 50 and preferably at least 70;
- Compositions have a UVAPF/SPF ratio of at least 1/3, and preferably at least 2/5; and/or
- Compositions have a UVA1/UV ratio of 0.7 or higher, preferably 0.75 or higher, and preferably 0.8 or higher.

"Makeup Result" as used herein relates to the visual impact of a composition when applied to a keratinous material such as the skin. The makeup result may relate to the apparent color of the product after application on a keratinous material or an optical effect such as shine, blurring of fine lines and imperfections, or hiding effect on pores or blemishes after the product is applied to the keratinous material.

"Long wear" as used herein refers to compositions where color or other apparent properties remains the same or substantially the same as at the time of application, as viewed by the naked eye, after an extended period of time or after a particular stress event such as water immersion or rubbing. "Long wear" may be evaluated by evaluating long wear properties by any method known in the art for evaluating such properties. For example, long wear may be evaluated by a test involving the application of a composition to keratinous material such as skin and evaluating the color of the composition after an extended period of time. For example, the color of a composition may be evaluated immediately following application to keratinous material such as skin and these characteristics may then be re-evaluated and compared after a certain amount of time. Further, these characteristics may be evaluated with respect to other compositions, such as commercially available compositions. "Long wear" may also be evaluated using vitro methods on non-keratinous substrates such as polymethylmethacrylate (PMMA), wherein properties such as color, transparency, or vitro SPF may be evaluated before and after a period of time or stressor such as water immersion, incubation at elevated temperatures, or an abrasive technique is applied.

"Natural" as in the phrase "natural compound" refers to any compound derived directly from a natural substance such as a plant without having undergone any chemical modification.

"Compound of natural origin" refers to any compound derived from a natural compound which has undergone one or more chemical modifications, for example by organic synthesis reaction, without the properties of the natural compound having been modified.

"Synthetic compound" refers to any compound which is not a natural compound or a compound of natural origin.

"Room temperature" means about 20-25° C.

"Atmospheric pressure" means about 760 mmHg, i.e. about 105 pascals.

"UV filter" and "sunscreen agent" are used interchangeably in this application.

"UV efficacy" and "UV efficiency" are used interchangeably in this application.

The compositions and methods of the present disclosure can comprise, consist of, or consist essentially of the essential elements and limitations of the disclosure described herein, as well as any additional or optional ingredients, components, or limitations described herein or otherwise useful. For example, the UV (ultraviolet) absorbing system of the compositions of the disclosure can "consist essentially of" bis-ethylhexyloxyphenol methoxyphenyl triazine."

For purposes of the present disclosure, the "basic and novel property" associated with compositions, components and methods which "consist essentially of" identified ingredients or actions is "UVA protection indicated by UVAPF/SPF and UVA1/UV ratios."

Compositions of the present disclosure may be in any form suitable for use as a personal care composition, such as that of a stick, a paste, a cream. These compositions can be used for any personal care purpose in cosmetic and/or dermatological products such as, for example, a sunscreen, a foundation, lip balms, lipsticks, concealers, mascaras, leave-in hair products, etc.

Referred to herein are trade names for materials including, but not limited to, materials such as polymers and optional components. Materials are not intended to be limited by materials described and referenced by a certain trade name herein. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

All U.S. patents or patent applications disclosed herein are expressly incorporated by reference in their entirety.

Composition

Bis-Ethylhexyloxyphenol Methoxyphenyl Triazine

According to the present disclosure, compositions comprising a UV (ultraviolet) absorbing system comprising 4-bis-{[4-(2-ethyl hexyloxy)-2-hydroxy]-phenyl]-6-(4-methoxyphenyl)-1,3,5-triazine (INCI name: Bis-Ethylhexyloxyphenol Methoxyphenyl Triazine) are provided.

According to preferred embodiments, the UV absorbing system comprises at least 5% by weight of the bis-ethylhexyloxyphenol methoxyphenyl triazine, preferably at least 15% by weight of the bis-ethylhexyloxyphenol methoxyphenyl triazine, preferably at least 20% by weight of the bis-ethylhexyloxyphenol methoxyphenyl triazine, preferably at least 30% by weight of the bis-ethylhexyloxyphenol methoxyphenyl triazine, preferably at least 40% by weight of the bis-ethylhexyloxyphenol methoxyphenyl triazine, preferably at least 50% by weight of the bis-ethylhexyloxyphenol methoxyphenyl triazine, preferably at least 70% by weight of bis-ethylhexyloxyphenol methoxyphenyl triazine, preferably at least 80% by weight of the bis-ethylhexyloxyphenol methoxyphenyl triazine, and preferably at least 90% by weight of the bis-ethylhexyloxyphenol methoxyphenyl triazine, with all weights being based on the total weight of the UV absorbing system. "UV absorbing system" contains all organic UV filters and/or mineral UV filters present in the composition.

According to preferred embodiments, bis-ethylhexyloxyphenol methoxyphenyl triazine is present in compositions of the present disclosure in a UV absorbing effective amount such as, for example, from about 0.1% to about 10% by weight with respect to the total weight of the composition, from about 1% to about 10% by weight, from about 2.5% to about 8% by weight, and from about 4% to about 6% by weight, including all ranges and subranges therebetween such as, for example, from about 4.5% to about 10% by weight, and from about 1% to about 8% by weight, from about 1% to about 6% by weight, from about 5.5% to about 8% by weight, from about 5.7% to about 9% by weight, etc., with all weights being based on the total weight of the composition.

Additional Organic UV Filter(s)

According to preferred embodiments of the present disclosure, compositions comprising a UV absorbing system optionally further comprising at least one additional organic UV filter (in addition to bis-ethylhexyloxyphenol methoxyphenyl triazine) are provided. Such compositions may also optionally further comprise mineral UV filter(s) such as oxides of zinc, oxides of titanium, oxides of cerium, and mixtures thereof, if desired, although the compositions may also be "free of," "substantially free of," or "devoid of" mineral UV filter(s).

Additional organic UV filter(s) can be hydrophilic or lipophilic. "Hydrophilic organic UV filter" means a water-soluble organic UV filter or a water-dispersible (in colloidal form) organic UV filter. "Lipophilic organic UV filter" means a UV filter which is dissolved or dispersed in colloidal form in a liquid fatty phase.

Suitable organic UV filters can be selected from the following non-exhaustive list of compounds: cinnamic compounds; anthranilate compounds; Para-aminobenzoic acid compounds; salicylic compounds; dibenzoylmethane compounds; camphor compounds; benzophenone compounds; β,β-diphenylacrylate compounds; triazine compounds different from Bis-Ethylhexyloxyphenol Methoxyphenyl Triazine; benzotriazole compounds; benzalmalonate compounds including those mentioned in U.S. Pat. No. 5,624,663; benzimidazole derivatives; imidazoline compounds; bis-benzoazolyl compounds as described in patents EP669323 and U.S. Pat. No. 2,463,264; methylene bis-(hydroxyphenyl benzotriazole) compounds as described in applications U.S. Pat. Nos. 5,237,071, 5,166,355, GB2303549, DE 197 26 184 and EP893119; benzoxazole compounds as described in patent applications EP0832642, EP1027883, EP1300137 and DE10162844; polymer filters and silicone filters such as those described in particular in application WO-93/04665; dimers derived from -alkylstyrene such as those described in patent application DE19855649; 4,4-diarylbutadienes compounds as described in applications EP0967200, DE19746654, DE19755649, EP-A-1008586, EP1133980 and EP133981 and mixtures thereof. Preferably, the lipophilic organic UV filters are selected from salicylic compounds, dibenzoylmethane compounds, benzylidene camphor compounds; benzophenone compounds; triazine compounds different from Bis-Ethylhexyloxyphenol Methoxyphenyl Triazine; benzotriazole compounds; as well as other categories of compounds identified herein; and mixtures thereof.

Specific reference can be made to suitable salicylic compounds including Homosalate (homomentyl salicylate), for example marketed under the trademark "Eusolex HMS" by Rona/EM Industries; and ethylhexyl salicylate, for example marketed under the trademark "Neo Heliopan OS" by Symrise; and glycol salicylate. Other examples of salicylate compounds include phenyl salicylate; dipropyleneglycol salicylate, for example marketed under the trademark "Dipsal" by Scher; and TEA salicylate, for example marketed under the trademark "Neo Heliopan TS" by Symrise.

Examples of suitable β,β-Diphenylacrylate compounds include Octocrylene, for example marketed under the trademark "Uvinul N539" by BASF; and Etocrylene, for example marketed under the trademark "Uvinul N35" by BASF.

Suitable anthranilic compounds can include menthyl anthranilates, for example marketed under the trademark "Neo Heliopan MA" by Symrise.

Examples of dibenzoylmethane compounds include Butyl methoxydibenzoylmethane, for example marketed under the trademark "Parsol 1789" by DSM; and isopropyl dibenzoylmethane.

Suitable cinnamic compounds include Ethylhexyl methoxycinnamate, for example marketed under the trademark "Parsol MCX" by DSM; isopropyl methoxycinnamate; isopropoxy methoxycinnamate; isoamyl methoxycinnamate, for example marketed under the trademark "Neo Heliopan E 1000" by Symrise; cinoxate (2-ethoxyethyl-4-methoxy cinnamate); DEA methoxycinnamate; diisopropyl methylcinnamate; and glyceryl ethylhexanoate dimethoxycinnamate.

Examples of camphor compounds include benzylidenecamphor derivatives: 3-benzylidene camphor, for example marketed under the trademark "Mexoryl SD" by Chimex; 4-methylbenzylidene camphor, for example marketed under the trademark "Eusolex 6300" by Merck; benzylidene camphor sulfonic acid, for example marketed under the trademark "Mexoryl SL" by Noveal; camphor benzalkonium methosulfate, for example marketed under the trademark "Mexoryl SO" by Noveal; terephthalylidene dicamphor sulfonic acid, for example marketed under the trademark "Mexoryl SX" by Noveal; and polyacrylamidomethyl benzylidene camphor, for example marketed under the trademark "Mexoryl SW" by Noveal.

Suitable benzophenone compounds include benzophenone-1 (2,4-dihydroxybenzophenone), such as that marketed under the trademark "Uvinul 400" by BASF; benzophenone-2 (Tetrahydroxybenzophenone), such as that marketed under the trademark "Uvinul D50" by BASF; Benzophenone-3 (2-hydroxy-4-methoxybenzophenone) or oxybenzone, such as that marketed under the trademark "Uvinul M40" by BASF; benzophenone-4 (hydroxymethoxy benzophonene sulfonic acid), such as that marketed under the trademark "Uvinul MS40" by BASF; benzophenone-5 (Sodium hydroxymethoxy benzophenone Sulfonate); benzophenone-6 (dihydroxy dimethoxy benzophenone); such as that marketed under the trademark "Helisorb 11" by Norquay; benzophenone-8, such as that marketed under the trademark "Spectra-Sorb UV-24" by American Cyanamid; benzophenone-9 (Disodium dihydroxy dimethoxy benzophenonedisulfonate), such as that marketed under the trademark "Uvinul DS-49" by BASF; and benzophenone-12, and n-hexyl 2-(4-diethylamino-2-hydroxybenzoyl)benzoate (such as that marketed under the tradename UVINUL A+ by BASF).

Examples of triazine compounds include Diethylhexyl butamido triazone, such as that marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine, such as that marketed under the trademark "TINOSORB S" by BASF, and ethylhexyl triazone, such as that marketed under the trademark "UVTNUL T150" by BASF.

Suitable benzotriazole compounds include phenylbenzotriazole derivatives: 2-(2H-benzotriazole-2-yl)-6-dodecyl-4-methylpheno, branched and linear; and those described in U.S. Pat. No. 5,240,975.

Suitable benzalmalonate compounds include Dineopentyl 4'-methoxybenzalmalonate, and polyorganosiloxane comprising benzalmalonate functional groups, such as polysilicone-15, such as that marketed under the trademark "Parsol SLX" by Hoffmann-LaRoche.

Examples of benzimidazole compounds include, in particular, phenylbenzimidazole derivatives such as phenylbenzimidazole sulfonic acid, such as that marketed in particular under the trademark "Eusolex 232" by Merck, and disodium phenyl dibenzimidazole tetrasulfonate, such as that marketed under the trademark "Neo Heliopan AP" by Symrise.

Suitable imidazoline compounds include Ethylhexyl dimethoxybenzylidene dioxoimidazoline propionate.

Examples of bis-benzoazolyl compounds include the compounds described in EP-669,323 and U.S. Pat. No. 2,463,264.

Suitable para-aminobenzoic acid compounds include PABA (p-aminobenzoic acid), ethyl PABA, Ethyl dihydroxypropyl PABA, pentyl dimethyl PABA, ethylhexyl dimethyl PABA, such as that marketed under the trademark "Escalol 507" by ISP, glyceryl PABA, and PEG-25 PABA, such as that marketed under the trademark "Uvinul P25" by BASF.

Suitable methylene bis-(hydroxyphenylbenzotriazol) compounds include 2,2'-methylenebis[6-(2H-benzotriazol- 2-yl)-4-methyl-phenol], such as that marketed under the trademark "Mixxim BB/200" by Fairmount Chemical, 2,2'-methylenebis[6-(2H-benzotriazol-2-yl)-4-(1,1,3,3-tetramethylbutyl)phenol], such as that marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, such as that marketed under the trademark "Silatrizole" by Rhodia Chimie or—"Mexoryl XL" by L'Oréal.

Examples of benzoxazole compounds include 2,4-bis[5-I(dimethylpropyl)benzoxazol-2-yl-(4-phenyl)imino]-6-(2-ethylhexyl)imino-1,3,5-triazine, such as that marketed under the trademark of Uvasorb K2A by Sigma 3V.

Suitable examples of screening polymers and screening silicones include the silicones described in WO 93/04665.

Suitable dimers derived from a-alkylstyrene include the dimers described in DE-19855649.

Examples of 4,4-Diarylbutadiene compounds include 1,1-dicarboxy(2,2'-dimethylpropyl)-4,4-diphenylbutadiene.

According to preferred embodiments, compositions of the present disclosure further comprise at least one additional organic UV filter selected from the group consisting of Avobenzone (butyl methoxydibenzoylmethane), Octisalate (ethylhexyl salicylate), Ensulizole (Phenylbenzimidazole sulfonic acid), Homosalate, Octocrylene, and mixtures thereof. In such embodiments, the UV absorbing system can "consist of" or "consist essentially of" (1) bis-ethylhexyloxyphenol methoxyphenyl triazine and (2) at least one organic UV filter selected from the group consisting of Avobenzone (butyl methoxydibenzoylmethane), Octisalate (ethylhexyl salicylate), Ensulizole (Phenylbenzimidazole sulfonic acid), Homosalate, Octocrylene, and mixtures thereof.

According to other preferred embodiments, however, compositions of the present disclosure are "free of," "substantially free of," or "devoid of" as defined above of one or more of additional organic UV filters selected from the group consisting of Avobenzone (butyl methoxydibenzoylmethane), Octisalate (ethylhexyl salicylate), Ensulizole (Phenylbenzimidazole sulfonic acid), Homosalate, and Octocrylene, preferably two or more, preferably three or more, preferably four or more, or preferably all five of these sunscreen agents.

According to preferred embodiments, compositions of the present disclosure are "free of," "substantially free of," or "devoid of" as defined above of one or more of additional organic UV filters selected from the group consisting of OXYBENZONE (benzophenone-3), OCTINOXATE (Ethylhexyl methoxycinnamate), ETHYLHEXYL TRIAZONE, DROMETRIZOLE TRISILOXANE, METHYLENE BIS-BENZOTRIAZOLYL TETRAMETHYLBUTYL PHENOL, DIETHYLAMINO HYDROXY BENZOYL HEXYL BENZOATE, DIETHYLHEXYL BUTAMIDO TRIAZONE, ISOAMYL P-METHOXYCINNAMATE, POLYSILICONE-15, 4-METHYLBENZYLIDENE CAMPHOR, DISODIUM PHENYL DIBENZIMIDAZOLE TETRASULFONATE, METHOXYPROPYLAMINO CYCLOHEXENYLIDENE ETHOXYETHYLCYANOACET ATE, preferably two or more, preferably three or more, preferably four or more, etc., and preferably "free of," "substantially free of," or "devoid of" all of these sunscreen agents.

According to preferred embodiments, compositions of the present disclosure are "free of," "substantially free of," or "devoid of" as defined above of OXYBENZONE (benzophenone-3) and/or OCTINOXATE (Ethylhexyl methoxycinnamate).

Preferably, if present, the at least one additional organic UV filter is preferably present in compositions of the present disclosure in an amount of at least about 1% by weight, preferably at least about 5% by weight, preferably at least about 10% by weight, preferably at least about 12.5% by weight, and preferably at least about 15% by weight, with the upper end of the range of additional UV filter present preferably being about 40% by weight (e.g., about 1-40%, about 10-40%, about 12.5-40%, etc.), preferably about 30% by weight (e.g., about 5-30%, about 10-30%, about 15-30%, etc.), preferably about 25% by weight (e.g., about 5-25%, about 10-25%, about 15-25%, etc.), and preferably about 20% by weight (e.g., about 1-20%, about 5-20%, about 10-20%, etc.), with all weights being based on the total weight of the composition.

According to preferred embodiments, bis-ethylhexyloxyphenol methoxyphenyl triazine and the at least one additional organic UV filter, if present, are present in compositions of the present disclosure in a weight % ratio of preferably about 10:1 to about 1:10, preferably about 5:1 to about 1:5, preferably about 3:1 to about 1:3, and preferably about 2:1 to about 1:2, including all ranges and subranges therebetween, such as for example 5:1 to 2:1, 1:2 to 5:1, 8:1 to 1.5:1, 1:1.5 to 1:8, etc, with all weights being based on the weight % of bis-ethylhexyloxyphenol methoxyphenyl triazine and weight % of additional organic UV filter present in the composition. Preferably, a higher weight % of additional organic UV filter is present in the compositions than of bis-ethylhexyloxyphenol methoxyphenyl triazine.

According to preferred embodiments, compositions of the present disclosure comprise 10% or less by weight relative to the total weight of composition of additional UV filters (including mineral UV filters), preferably less than 7.5% by weight relative to the total weight of composition, preferably less than 5% by weight relative to the total weight of composition, preferably less than 3% by weight relative to the total weight of composition, and preferably less than 1% by weight relative to the total weight of composition.

According to preferred embodiments, compositions of the present disclosure comprise 10% or less by weight relative to the total weight of composition of additional organic UV filters, preferably less than 7.5% by weight relative to the total weight of composition, preferably less than 5% by weight relative to the total weight of composition, preferably less than 3% by weight relative to the total weight of composition, and preferably less than 1% by weight relative to the total weight of composition.

According to preferred embodiments, the UV absorbing system of compositions of the present disclosure can "consist of" or "consist essentially of" (1) bis-ethylhexyloxyphenol methoxyphenyl triazine and (2) optionally additional organic UV filters.

According to preferred embodiments, this disclosure contemplates omitting one or more of any of the specific UV filters discussed above from the UV absorbing system of compositions of the present disclosure. By way of example, octocrylene and/or octinoxate can be omitted from the compositions. Similar omission of one or more of any of the specific UV filters discussed is thus contemplated.

Lipophilic Acrylic Polymer

According to the present disclosure, emulsion compositions comprising at least one lipophilic acrylic polymer are provided, wherein the lipophilic acrylic polymer comprises monomer units of formulae (A) and (B):

[chem 1]

(A)

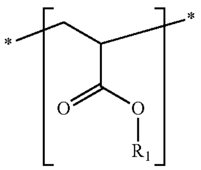

(B)

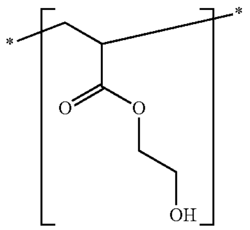

in which:

$R_1$, independently at each instance, is chosen from alkyl or alkenyl radicals, and at least 60% by weight of the R1 groups are radicals chosen from stearyl and behenyl radicals, the percentage by weight relating to the sum of all the R1 groups present in the polymer, and the weight ratio of the sum of all the hydroxyethyl acrylate units to the sum of all the acrylate units bearing the R1 group is from 1:30 to 1:1, and the sum of the total of units A and B is at least 95% by weight relative to the total weight of the polymer.

Preferably, $R_1$ is constituted of alkyl radicals, preferably of C16-C22 alkyl radicals, and preferably of stearyl (C18) radicals or of behenyl (C22) radicals.

Preferably, at least 70% by weight of the R1 groups are stearyl or behenyl radicals, preferentially at least 80% by weight and more preferentially at least 90% by weight.

According to one preferred embodiment, all the R1 groups are behenyl radicals.

According to another preferred embodiment, all the R1 groups are stearyl radicals.

Preferably, the weight ratio of the sum of all the hydroxyethyl acrylate units to the sum of all the acrylate units bearing the R1 group is from 1:15 to 1:1, preferably from 1:10 to 1:4.

Advantageously, the polymer units present in the polymer are constituted of the units (A) and (B) previously described.

The polymer preferably has a number-average molecular weight Mn ranging from 2000 to 9000 g/mol, preferably from 5000 to 9000 g/mol. The number-average molecular weight may be measured via the gel permeation chromatography method, for example according to the method described below.

The sample is prepared by preparing a solution of the polymer at 10 mg/ml in tetrahydrofuran. The sample is placed in an oven at 54° C. for 10 minutes and then in an oscillating shaker for 60 minutes to aid dissolution. After visual inspection, the sample appeared to be totally dissolved in the solvent.

The sample prepared is analyzed using two polypore 300×7.5 mm columns manufactured by Agilent Technologies, a Waters 2695 chromatographic system, a tetrahydrofuran mobile phase and detection by refractive index. The sample is filtered through a 0.45 μm nylon filter, before being injected into the liquid chromatograph. The standards used for the calibration are the Easi Vial narrow polystyrene (PS) standards from Agilent Technologies. Polystyrene standards ranging from 2 520 000 to 162 daltons can be used for the calibration.

The system is equipped with a PSS SECcurity 1260 RI detector. The polystyrene calibration curve is used to determine the average molecular weight. The recording of the diagrams and the determination of the various molecular weights can be performed by the Win GPC Unichrom 81 program.

Preferably, the polymer has a melting point ranging from 40° C. to 70° C., preferably from 45° C. to 67° C. The melting point is measured by differential scanning calorimetry (DSC), for example according to methods based on standards ASTM E791 and ASTM D 34182 and the DSC calibration is performed according to standard ASTM E 9672.

According to preferred embodiments, when the polymer is such that at least 60% by weight of the $R_1$ groups are stearyl radicals, then the polymer preferably has a melting point of from 40° C. to 60° C., preferably from 45° C. to 55° C.

According to preferred embodiments, when the polymer is such that at least 60% by weight of the R1 groups are behenyl radicals, then the polymer has a melting point of from 60° C. to 70° C., preferably from 63° C. to 67° C.

The polymer of the present disclosure can be prepared by polymerization of a monomer having the formula below:

$$CH2{=}CH{-}COO{-}R1,$$

R1 having the meaning previously described, and of 2-hydroxyethyl acrylate.

The polymerization may be performed according to known methods, such as solution polymerization or emulsion polymerization.

The polymerization is, for example, described in document US 2007/0264204, the entire contents of which is hereby incorporated by reference.

According to preferred embodiments, the at least one lipophilic acrylic polymer is present in compositions of the present disclosure in an amount (active material) of from 0.05 to 10% by weight, relative to the total weight of the composition, preferably from 0.1 to 5% by weight, and preferably from 0.2 to 2% by weight, including all ranges and subranges therebetween.

C12-C24 Fatty Acid Esters of a C2-C24 Polyol

According to the present disclosure, emulsion compositions comprising at least one C12-C24 fatty acid ester of a $C_2$-$C_{24}$ polyol are provided. Preferably, the at least one $C_{12}$-$C_{24}$ fatty acid ester of a $C_2$-$C_{24}$ polyol is at least one $C_{16}$-$C_{18}$ fatty acid ester of glycerol.

According to preferred embodiments, the $C_{12}$-$C_{24}$ fatty acid for the at least one $C_{12}$-$C_{24}$ fatty acid ester of a $C_2$-$C_{24}$ polyol can be a saturated or unsaturated acid such as, for example, stearic acid, oleic acid, palmitic acid, etc.

For the purposes of the present invention, the term "polyol" means any organic molecule including at least two free hydroxyl groups.

According to preferred embodiments, the polyol for the at least one C12-C24 fatty acid ester of a C2-C24 polyol can be a compound of linear, branched or cyclic structure, saturated or unsaturated alkyl type, bearing on the alkyl at least two OH functions, preferably at least three OH functions. Preferably, the polyol for the at least one C12-C24 fatty acid ester of a C2-C24 polyol preferably has 3 to 16 carbon atoms.

Preferably, the polyol is chosen, for example, from the group consisting of ethylene glycol, pentaerythritol, trimethylolpropane, propylene glycol, 1,3-propanediol, butylene glycol, isoprene glycol, pentylene glycol, hexylene glycol, polyglycerin-3, glycerol, and mixtures thereof. Preferably, the polyol is selected from 1,3-propanediol, polyglycerin-3, glycerol, pentylene glycol, and mixtures thereof. Preferably, the polyol is glycerol.

By way of examples of C12-C24 fatty acid esters of glycerol, mention may be made of glyceryl laurate, glyceryl oleate, glyceryl stearate, glyceryl palmitate, and mixtures thereof. As commercially available products, mention may be made of glyceryl stearate, such as the product sold under the name Tegin MO by Evonik Goldschmidt, and glyceryl laurate, such as the product sold under the name Imwitor 3120 by Hiils, and monoglyceride stearates (INCI name: Glyceryl Stearate), for example sold under the name Dimodan HP by Danisco, or those sold under the name Tegin 90 by Evonik Goldschmidt.

Preferably, the C12-C24 fatty acid ester of glycerol is glyceryl stearate.

According to preferred embodiments, the at least one C12-C24 fatty acid ester(s) of a C2-C24 polyol is present in compositions of the present disclosure in an amount (active material) of from 0.1% to 2% by weight, and preferably from 0.2% to 0.8% by weight, with all weights being with respect to the total weight of the composition, including all ranges and subranges therebetween.

Carboxylic or Carboxylate Anionic Surfactants Chosen from Fatty-Chain Amino acids and Salts Thereof According to the present disclosure, emulsion compositions comprising at least one carboxylic or carboxylate anionic surfactant selected from the group consisting of amino acids modified with at least one $C_8$-$C_{30}$ hydrocarbon-based chain, preferably a $C_8$-$C_{24}$ hydrocarbon-based chain, and salts thereof, are provided. The term "hydrocarbon-based chain" means a linear or branched, saturated or unsaturated, organic group constituted mainly of hydrogen atoms and carbon atoms, in which one or more carbon atoms can be replaced with an oxygen atom or a nitrogen atom. As examples of $C_8$-$C_{30}$ hydrocarbon-based chains, mention may be made of $C_8$-$C_{30}$ acyl radicals.

Exemplary amino acids include, but are not limited to, alanine, arginine, aspartic acid, glutamic acid, glycine, isoleucine, leucine, lysine, phenylalanine, serine, tyrosine, valine and sarcosine.

More specifically mention may be made of the following compounds: dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alaninate, lauroyl β-alaninate, lauroyl methyl β-alaninate, myristoyl β-alaninate, potassium lauroyl methyl β-alaninate, sodium cocoyl alaninate, sodium cocoyl methyl β-alaninate and sodium myristoyl methyl β-alaninate palmitoyl glycinate, sodium lauroyl glycinate, sodium cocoyl glycinate, sodium myristoyl glycinate, potassium lauroyl glycinate, potassium cocoyl glycinate, potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate ammonium lauroyl sarcosinate, sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate, and mixtures thereof.

According to preferred embodiments, the at least one carboxylic or carboxylate anionic surfactant is selected from compounds having the following structure:

[chem 2]

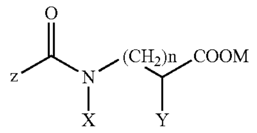

in which:

Z represents a saturated or unsaturated, linear or branched hydrocarbon-based group comprising from 8 to 24 carbon atoms, preferably from 8 to 22 carbon atoms, X is a hydrogen atom or a methyl group;

n is equal to 0 or to 1;

Y is a group chosen from a hydrogen atom and a —CH3, —CH(CH3)2, —CH2CH(CH3)2, —CH(CH3)CH2CH3, —CH2C6H5, —CH2C2H40H, —CH2OH, —CH(OH)CH3, —(CH2)4NH2, —(CH2)3NHC(NH)NH2, —$CH_2C(O)O^-M^+$, —$(CH_2)_2C(O)OH$ and —$(CH_2)_2C(O)O^-M^+$ group; and M is a hydrogen atom or a cation such as sodium, potassium, ammonium or triethanolamine.

According to preferred embodiments, in formula 2:

Z represents a linear or branched C8-C22 alkyl or alkenyl group;

X is a hydrogen atom or a methyl radical;

n is equal to 0;

Y is a hydrogen atom, a —(CH2)2C(O)OH group or a —(CH2)2C(O)O-M+ group; and

M is a cation such as sodium, potassium, ammonium or triethanolamine.

According to preferred embodiments, the composition according to the present disclosure comprises at least one acyl glutamic acid (INCI name: acyl glutamic acid) or a salt thereof (acyl glutamates). Preferably, the acyl glutamic acid(s) is/are chosen from acyl glutamic acids in which the acyl group comprises from 8 to 30 carbon atoms, preferably from 10 to 24 carbon atoms, and preferably from 12 to 22 carbon atoms, such as, for example, lauroylglutamic acid, myristoylglutamic acid, palmitoylglutamic acid, stearoylglutamic acid, behenoylglutamic acid, olivoylglutamic acid, cocoylglutamic acid, and the salts of these acids, especially the salts of alkali metals such as Na, Li or K, preferably Na or K, the salts of alkaline-earth metals such as Mg, or the ammonium salts of said acids.

Exemplary salts of amino acids modified with at least one $C_8$-$C_{30}$ hydrocarbon-based chain include, but are not limited to, glutamate salts, and in particular dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate.

Preferably, the acyl glutamic acid(s) or a salt thereof is/are chosen from lauroylglutamic acids, cocoylglutamic acids, sodium stearoyl glutamate, potassium lauroyl glutamate, potassium cocoyl glutamate, sodium olivoyl glutamate and mixtures thereof. Preferably, the acyl glutamic acid or a salt thereof is sodium stearoyl glutamate. Such compounds are sold under the name Amisoft by Ajinomoto and, in particular, under the references Amisoft CA, Amisoft LA, Amisoft HS 11 PF, Amisoft MK-11, Amisoft LK-11 and Amisoft CK-11, or alternatively under the name Eumulgin SG by Cognis.

Mention may also be made of triethanolamine cocoyl glutamate sold under the name Amisoft CT12 by Ajinomoto, and triethanolamine lauroyl glutamate sold under the name Acylglutamate LT-12 by Ajinomoto.

As acyl glutamic acid salts, mention may also be made of sodium hydrogenated tallowoyl glutamate, such as the product sold under the reference Acylglutamate HS 11 by Ajinomoto and disodium hydrogenated tallow glutamate, such as the product sold under the reference Acylglutamate HS-21 by Ajinomoto.

Mention may also be made of commercial mixtures of surfactants comprising at least one glutamic acid derivative or a salt of said derivative, for instance the mixture of acyl glutamate salts such as Amisoft LS-22 sold by Ajinomoto.

According to preferred embodiments of the present disclosure, compositions of the present disclosure comprise the monosodium salt of n-stearoyl-L-glutamic acid (INCI name: sodium stearoyl glutamate), such as the product sold by Ajinomoto under the reference Amisoft HS 11 PF.

According to preferred embodiments, the at least one amino acid modified with at least one $C_8$-$C_{30}$ hydrocarbon-based chain, and/or salts thereof, is preferably present in compositions of the present disclosure in an amount of from 0.01% to 5% by weight, preferably from 0.01% to 2% by weight, preferably from 0.05% to 1% by weight, preferably from 0.1% to 0.8% by weight, and preferably from 0.1% to 0.5% by weight, all weights being with respect to the total weight of the composition, including all ranges and subranges therebetween.

$C_{12}$-$C_{24}$ Saturated Fatty Alcohols

According to preferred embodiments, compositions optionally further comprising at least one $C_{12}$-$C_{24}$ saturated fatty alcohol are provided. Preferably, the at least one $C_{12}$-$C_{24}$ saturated fatty alcohol is linear and/or comprises from 14 to 22 carbon atoms. Suitable examples included, but are not limited to, cetyl alcohol, stearyl alcohol, cetearyl alcohol, myristyl alcohol, lauryl alcohol, tridecyl alcohol, pentadecyl alcohol, hexadecyl alcohol, arachidyl alcohol and/or behenyl alcohol, with cetyl alcohol, stearyl alcohol and/or cetearyl alcohol being most preferred.

Commercially available cetyl alcohol includes, but is not limited to, those sold under the names Ecorol® 16/98 F and Ecorol® 16/98 P by Ecogreen Oleochemicals, Tegoalkanol® 16 by Evonik Goldschmidt, Lanette® 16 by Cognis, Vegarol® 1698 by VVF, Alkonat® 1698 P by Oxiteno, Cetyl Alcohol 98% MIN by Emery Oleochemicals, Ginol® 16 (98%) by Godrej Industries, Nacol® 16-98 by Sasol, Kalcol® 6098 by Kao and Acilol® 16 by Aegis Chemical.

Commercially available stearyl alcohol includes, but is not limited to, those sold under the names Tegoalkanol® 18 by Evonik Goldschmidt, Ecorol® 18/98 F and Ecorol® 18/98 P by Ecogreen Oleochemicals, Lanette® 18 by Cognis, Kalcol® 8098 by Kao, Acilol® 18 by Aegis Chemical, Nacol® 18-98 by Sasol and NAA® 45 by Nihon Yushi.

Commercially available cetearyl alcohol includes, but is not limited to, those sold under the names Ecorol® 68/50 F and Ecorol® 68/50 P by Ecogreen Oleochemicals, Lanette® O OR and Lanette® O OR Flakes by Cognis, Alkonat® 1618 C50 P by Oxiteno, Nafol® 16-18 EN by Sasol, Alcohol Cetoestearilico 50/50 by Industria Quimica Del Centro, Conol® 30 CK by New Japan Chemical, Cetylstearyl Alcohol 50:50 by Evonik Goldschmidt, Kalcol® 6850 by Kao, Vegarol® 1618 (50:50) by VVF and Ginol® 1618 50:50 OR by Godrej Industries.

Commercially available behenyl alcohol includes, but is not limited to, those sold under the names Lanette 22 by BASF.

Preferably, compositions of the present disclosure possess an alpha-gel structure, that is to say that it has a lamella phase, believed to be due to the presence of a surfactant and of a C12-C24 saturated fatty alcohol.

If present, the at least one C12-C24 saturated fatty alcohol is preferably present in compositions of the present disclosure in an amount of from 0.1% to 5% by weight, preferably from 0.2% to 3% by weight, and preferably from 0.5% to 2% by weight, all weights being based on the total weight of the composition, including all ranges and subranges therebetween.

Waxes

According to preferred embodiments, compositions of the present disclosure optionally further comprise at least one wax. "Wax" means a deformable or undeformable lipophilic compound, which is solid at ambient temperature (25° C.), with a reversible solid/liquid change of state, having a melting point of greater than or equal to 30° C., which may be up to 120° C. In particular, the waxes that are suitable for use in the disclosed compositions preferably have a melting point of greater than or equal to 60° C., preferably greater than or equal to 70° C.

The term "lipophilic compound" refers to a compound having an acid number and a hydroxyl number of less than 150 mg KOH/g.

Melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name MDSC 2920 by TA Instruments or the calorimeter sold under the name DSC Q100 by TA Instruments with the TA Universal Analysis software.

A measuring protocol is as follows:

A sample of 5 mg of wax placed in a crucible is subjected to a first temperature ramp passing from −20° C. to 100° C., at a heating rate of 10° C./minute, it is then cooled from 100° C. to −20° C. at a cooling rate of 10° C./minute and is finally subjected to a second temperature ramp passing from −20° C. to 100° C. at a heating rate of 5° C./minute. During the second temperature ramp, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes can be hydrocarbon waxes, silicone waxes and/or fluoro waxes, and can be of plant, animal, mineral and/or synthetic origin.

Preferably, if present, the wax(es) are present in the composition in a content ranging from 0.01% to 5% by weight, preferably from 0.1% to 3% by weight, and preferably from 0.2% to 2% by weight, relative to the total weight of the composition, including all ranges and subranges therebetween.

According to preferred embodiments, the composition in accordance with the present disclosure comprises at least one wax of plant origin.

According to preferred embodiments, the composition in accordance with the present disclosure comprises at least one jojoba ester wax. The jojoba ester wax may be in an unsaturated form of jojoba esters, which may be the entirely hydrogenated jojoba ester having the formula below:

[chem 3]

$$R^1—COO—CH_2—R^1$$

in which:

R1 is a CH3-(CH2)y group, y is equal to 16, 18, 20 or 22.

The jojoba ester wax can be obtained by hydrogenation of a jojoba wax ester (jojoba oil) having the formula below:

[chem 4]

$$CH_3—(CH_2)_7—CH{=}CH—CH_2—(CH_2)_X—\overset{\overset{\displaystyle O}{\|}}{C}—O—CH_2—(CH_2)_Y—CH_2—CH{=}CH—(CH_2)_7—CH_3$$

in which x and y are equal to 6, 8, 10 or 12.

The jojoba wax esters are composed of straight-chain monounsaturated fatty alcohols and of monounsaturated fatty acids. The only double bond is located in the middle (position n-9), starting from the methyl end group (—CH3) of the chain of the respective fatty acid or alcohol.

Such wax esters are composed of fatty alcohols and of fatty esters with an even number of carbon atoms, mainly 20 and 22 carbon atoms. The resulting material comprises esters having chain lengths of 38, 40, 42 and 44 carbon atoms, with a small amount of esters of 36 and 46 carbon atoms being present. The typical composition of the wax esters is indicated below.

TABLE 1

| Wax esters | | |
|---|---|---|
| (X, Y) | Chain length | typical % (surface by GPC) |
| (6, 6) | 36 | 1 |
| (6, 8) (8, 6) | 38 | 8 |
| (6, 10) (8, 8) (10, 6) | 40 | 39 |
| (10, 8) (8, 10) | 42 | 38 |
| (10, 10) | 44 | 13 |
| (12, 10) (10, 12) | 46 | 1 |

The jojoba wax ester can be derived from the seed of the jojoba plant (*Simmondsia chinensis*).

By way of examples of a jojoba wax ester, mention may be made of the product sold under the name Floraesters® 70 by International Flora Technologies Ltd, and the product sold under the name Jojoba Esters-70 by Vantage.

Preferably, if present, the jojoba ester wax is present in the composition in an amount ranging from 0.1% to 2% by weight, and preferably from 0.2% to 0.8% by weight relative to the total weight of the composition, including all ranges and subranges therebetween.

According to preferred embodiments, the composition in accordance with the present disclosure comprises at least one additional hydrocarbon-based wax in addition to the jojoba ester mentioned above. Suitable examples include, but are not limited to, beeswax, lanolin wax or Chinese insect wax, rice wax, carnauba wax, candelilla wax, ouricury wax, esparto grass wax, cork fibre wax, sugar cane wax, Japan wax, Berry wax, shellac wax and sumac wax, *Helianthus annuus* (sunflower) seed wax, montan wax, microcrystalline waxes, paraffins and ozokerite; use may in particular be made of polyethylene waxes, polymethylene waxes, waxes obtained by Fischer-Tropsch synthesis and waxy copolymers, and also esters thereof. Mention may in particular be made of beeswax, for example the product sold under the name White beeswax BR G889 by Koster Keunen, carnauba wax, for example sold under the name CeRauba T1 Bio by Baerlocher, *Helianthus annuus* (sunflower) wax sold under the name Sunflower Wax by Koster Keunen, or a mixture thereof. Preferably, compositions of the present disclosure comprise *Helianthus annuus* (sunflower) seed wax.

If present, the additional hydrocarbon-based wax is preferably present in the composition in an amount ranging from 0.05% to 5% by weight, preferably from 0.1% to 1% by weight and preferably from 0.1% to 0.5% by weight, relative to the total weight of the composition, including all ranges and subranges therebetween.

According to preferred embodiments, the composition in accordance with the present disclosure comprises a mixture of glyceryl stearate, sodium steroyl glutamate, cetearyl alcohol, jojoba esters and sunflower seed wax, having the INCI name Cetearyl Alcohol (and) Jojoba Esters (and) Glyceryl Stearate (and) Sodium Stearoyl Glutamate (and) *Helianthus Annuus* Seed Cera (and) Polyglycerin-3, sold under the name Emulium® Dolcea MB by Gattefosse.

According to preferred embodiments, the composition in accordance with the present disclosure comprises:

- bemotrizinol;
- at least one lipophilic acrylic polymer as defined previously;
- at least one C12-C24 saturated fatty alcohol;
- at least one C12-C24 fatty acid ester of glycerol;
- at least one carboxylic or carboxylate anionic surfactant chosen from amino acids modified with at least one C8-C24 hydrocarbon-based chain, and salts thereof; and
- at least one wax.

According to preferred embodiments, the composition in accordance with the present disclosure comprises:

- bemotrizinol;
- at least one lipophilic acrylic polymer as defined previously;

at least one C12-C24 saturated fatty alcohol;

at least one C12-C24 fatty acid ester of glycerol;

at least one carboxylic or carboxylate anionic surfactant chosen from amino acids modified with at least one C8-C24 hydrocarbon-based chain, and salts thereof; and at least one jojoba ester wax.

According to preferred embodiments, the composition in accordance with the present disclosure comprises:

bemotrizinol;

at least one lipophilic acrylic polymer as defined previously;

at least one C12-C24 saturated fatty alcohol;

at least one C12-C24 fatty acid ester of glycerol;

at least one acyl glutamic acid (INCI name: acyl glutamic acid) or a salt thereof (acyl glutamates), the acyl group being a C10-C30, preferably C12-C22, acyl group; and at least one jojoba ester wax.

According to preferred embodiments, the composition in accordance with the present disclosure comprises:

bemotrizinol;

at least one lipophilic acrylic polymer as defined previously;

at least one C12-C24 saturated fatty alcohol;

at least one C12-C24 fatty acid ester of glycerol;

at least one carboxylic or carboxylate anionic surfactant chosen from amino acids modified with at least one C8-C24 hydrocarbon-based chain, and salts thereof;

at least one jojoba ester wax; and at least one *Helianthus annuus* (sunflower) seed wax.

According to preferred embodiments, the composition in accordance with the present disclosure comprises:

bemotrizinol;

at least one lipophilic acrylic polymer as defined previously;

at least one C12-C24 saturated fatty alcohol;

at least one C12-C24 fatty acid ester of glycerol;

at least one acyl glutamic acid (INCI name: acyl glutamic acid) or a salt thereof (acyl glutamates), the acyl group being a C10-C30, preferably C12-C22, acyl group;

at least one jojoba ester wax; and at least one *Helianthus annuus* (sunflower) seed wax.

According to preferred embodiments, the composition in accordance with the present disclosure is a fluid composition for skin care, in the form of an oil-in-water emulsion, comprising, relative to the total weight of the composition:

(i) bemotrizinol;

(ii) from 0.05% to 10% by weight of a lipophilic acrylic polymer comprising monomer units of formulae (A) and (B):

[chem 1]

(A)

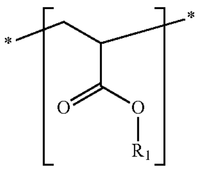

-continued (B)

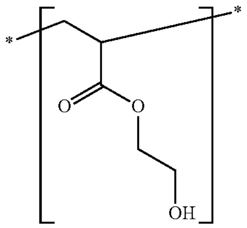

in which:

R1, independently at each instance, is chosen from alkyl or alkenyl radicals, and at least 60% by weight of the R1 groups are radicals chosen from stearyl and behenyl radicals, the percentage by weight relating to the sum of all the R1 groups present in the polymer, and the weight ratio of the sum of all the hydroxyethyl acrylate units to the sum of all the acrylate units bearing the R1 group ranges from 1:30 to 1:1, and the sum of the total of units A and B is at least 95% by weight relative to the total weight of the polymer;

(iii) from 0.2% by weight to 0.8% by weight of at least one jojoba ester wax of formula 3:

[chem 3]

$$R^1—COO—CH_2—R^1$$

where R1 is CH3-(CH2)y-, y is 16, 18, 20 or 22;

(iv) from 0.5% by weight to 2% by weight of at least one C12-C24 saturated fatty alcohol chosen from cetyl alcohol, stearyl alcohol and cetearyl alcohol;

(v) from 0.2% by weight to 0.8% by weight of at least one C12-C24 fatty acid ester of glycerol chosen from glyceryl laurate, glyceryl oleate, glyceryl stearate, glyceryl palmitate, and a mixture thereof; and (vi) from 0.1% by weight to 0.5% by weight of at least one surfactant chosen from acyl glutamic acids (INCI name: acyl glutamic acid) and salts thereof (acyl glutamates), the acyl group being a C10-C30, preferably C12-C22, acyl group; even more preferentially, it is the stearoyl radical.

Oil

According to preferred embodiments of the present disclosure, compositions further comprising at least one oil are provided. "Oil" means a substance which is hydrophobic and lipophilic, and is a liquid at about room temperature (20 to 25° C.) and about atmospheric pressure (760 mm Hg).

Suitable include volatile and/or non-volatile oils. Such oils can be any acceptable oil including but not limited to silicone oils and/or hydrocarbon oils.

According to certain embodiments, the compositions of the present disclosure preferably comprise one or more volatile silicone oils. Examples of such volatile silicone oils include linear or cyclic silicone oils having from 2 to 7 silicon atoms, these silicones being optionally substituted with alkyl or alkoxy groups of 1 to 10 carbon atoms. Specific oils that may be used in the disclosure include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present disclosure. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present disclosure, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

According to certain embodiments of the present disclosure, the composition comprises at least one non-volatile oil. Examples of non-volatile oils that may be used in the present disclosure include, but are not limited to, polar oils such as, for example:

esters and ethers, in particular fatty acids, such as oils of formulas R1 COOR2, wherein R 1 represents the remainder of a fatty acid having from 8 to 29 carbon atoms, and R 2 represents a hydrocarbon chain, branched or not, containing from 3 to 30 carbon atoms, such as for example Purcellin oil, isononyl isononanoate, isopropyl myristate, ethyl-2-hexyl palmitate, octyl-2-dodecyl stearate, octyl-2-dodecyl erucate, isostearyl isostearate; hydroxylated esters such as isostearyl lactate, octylhydroxystearate, octyldodecyl hydroxystearate, diisostearylmalate, triisocetyl citrate, heptanoates, octanoates, fatty alcohol decanoates; polyol esters, such as propylene glycol dioctanoate, neopentylglycol diheptanoate and diethylene glycol diisononanoate; tryiglycerides such as caprylic/capric acid triglycerides, for instance those sold by the company Stearineries Dubois or those sold under the names Miglyol 810, 812 and 818 by the company Dynamit Nobel; and esters of pentaerythritol such as pentaerythrityl tetraisostearate or dipentaerythrityl pentaisononanoate;

ethers containing from 10 to 40 carbon atoms;

liquid C8 to C26 fatty alcohols, for instance oleyl alcohol, cetyl alcohol, stearyl alcohol, octyldodecanol, and cetearly alcohol;

hydrocarbon oils of animal origin, such as perhydrosqualene;

hydrocarbon oils of vegetable origin, such as liquid triglycerides of fatty acids having from 4 to 10 carbon atoms such as triglycerides of heptanoic or octanoic acids or, for example, sunflower, corn, soybean, squash, grape seed, sesame, hazelnut, apricot, macadamia, ara, sunflower oil, castor oil, avocado, triglycerides of caprylic/capric acids such as those sold by the company Stearineries Dubois or those sold under the names Miglyol 810, 812 and 818 by the company Dynamit Nobel, coco-caprylate/caprate (esterified oil from coconut oil), jojoba oil, shea butter oil; and mixtures thereof.

Further, examples of non-volatile oils that may be used in the present disclosure include, but are not limited to, non-polar oils such as branched and unbranched hydrocarbons, in particular Vaseline (petrolatum), paraffin oil, squalane, squalene, hydrogenated polyisobutene, hydrogenated polydecene, polybutene, mineral oil, pentahydrosqualene, and mixtures thereof.

According to certain embodiments of the present disclosure, the compositions of the present disclosure comprise at least one non-volatile silicone oil. Suitable examples of such silicone oils include, but are not limited to, non-volatile silicone fluids such as, for example, polyalkyl (aryl) siloxanes. Suitable polyalkyl siloxanes include, but are not limited to, polydimethyl siloxanes, which have the CTFA designation dimethicone, polydiethyl siloxane, phenyl trimethicone, trimethyl pentaphenyl trisiloxane, phenyldimethicone, phenyltrimethylsiloxydiphenylsiloxane, diphenyldimethicone, and diphenylmethyldiphenyltrisiloxane and those siloxanes disclosed in U.S. patent application publication no. 2004/0126350, the entire disclosure of which is hereby incorporated by reference. Specific examples of suitable high viscosity silicone oils include, but are not limited to, 15 M 30 from PCR (500 cSt) or Belsil PDM 1000 (1 000 cSt) from Wacker and Dow Corning 200 (350 cSt) (the values in parenthesis represent viscosities at 25° C.).

Particularly preferred oils include, but are not limited to, one or more of the following: Diisopropyl Sebacate, C12-15 Alkyl Benzoate, Phenethyl Benzoate, Isopropyl Lauroyl Sarcosinate, Diisopropyl Adipate, Dibutyl Adipate, Dicaprylyl Carbonate, Dicaprylate/Dicaprate, Coco Glycerides, Caprylic/capric triglyceride, Isopropyl Myristat, Isopropyl Palmitate, Coco Caprylate/Caprate, Ethylhexyl Palmitate, Isononyl isononanoate, Octyl dodecanol, Isohexadecane, isododecane, Dicaprylyl Ether, C15-19 Alkane, and mixtures thereof.

According to preferred embodiments, the at least one oil is/are present in the compositions of the present disclosure in an amount ranging from about 1% to about 50% by weight, more preferably from about 5 to about 40% by weight, and preferably from about 10% to about 35% by weight, based on the total weight of the composition, including all ranges and subranges within these ranges such as, for example, 15% to 40%, 20% to 45%, etc.

Aqueous Phase

According to the present disclosure, compositions comprising an aqueous phase comprising water are provided. Preferably, when the compositions of the present disclosure contain water, they are in the form of an emulsion containing an external aqueous phase such as an oil-in-water emulsion (O/W) or a water-in-oil-in-water emulsion (O/W/O). Preferably, when in the form of an emulsion, the oil phase can contain silicone oils (e.g., Si/W or W/Si emulsion) or hydrocarbon oils. When present, water is preferably present in an amount of from about 10% to about 80% by weight, preferably from about 20% to about 70% by weight, preferably from about 35% to about 65% by weight, including all ranges and subranges therebetween, all weights being based on the total weight of the composition.

The aqueous phase may optionally further comprise at least one water-soluble organic solvent which is liquid at room temperature and atmospheric pressure. For example, such at least one water-soluble organic solvent may include:

Triethyl citrate;

C1-C5 monoalcohols having a C1-C5 alkane chain and a single hydroxyl function (OH). Suitable C1-C5 monoalcohols include methanol, ethanol, propanol, isopropanol, butanol and mixtures thereof;

polyols (compounds having 2 or more hydroxyl groups) having, for example from 2 to 20 carbon atoms, preferably from 2 to 6 carbon atoms, such as for example glycerol, diglycerol, propylene glycol, isoprene glycol, dipropylene glycol, butylene glycol, hexylene glycol, 1,3-propanediol, pentylene glycol, simple sugars, and water-soluble polyalkylene glycols;

and mixtures thereof.

According to preferred embodiments, the at least one water-soluble organic solvent is selected from the group consisting of ethanol, dipropylene glycol, butylene glycol, propanediol and propylene glycol, and mixtures thereof.

If present, the water-soluble organic solvent(s) is/are preferably present in compositions of the present disclosure in an amount ranging from about 0.5 to about 40% by weight, preferably from about 3 to about 30% by weight, and preferably from about 5% to about 20% by weight relative to the total weight of the composition, including all ranges and subranges therebetween such as, for example, 2% to 15%, 2% to 25%, 7.5% to 30%, etc.

Additional Optional Ingredients

Compositions of the present disclosure may also optionally further include at least one additive or auxiliary commonly used in cosmetic compositions and known to a person skilled in the art as being capable of being incorporated into such compositions. Such additives or auxiliaries may be chosen from additional film formers, additional surfactants, coloring agents (e.g., dyes and pigments), waxes, thixotropic agents (e.g., clays), fillers, preservatives, fragrances, antioxidants, agents for combating free radicals, spreading agents, dispersing agents, antifoaming agents, neutralizing agents, stabilizing agents, active principles chosen from essential oils, moisturizing agents, vitamins, actives, proteins, ceramides, plant extracts, fibers, and the like, wetting agents and their mixtures. Although, preferably, compositions of the present disclosure are "free of," "substantially free of," or "devoid of" such additives.

A person skilled in the art will take care to select the optional additional additives and/or the amount thereof such that the advantageous properties of the composition according to the disclosure are not, or are not substantially, adversely affected by the envisaged addition.

Needless to say, the composition of the disclosure should be cosmetically or dermatologically acceptable, i.e., it should contain a non-toxic physiologically acceptable. The composition may be in any galenic form normally employed in the cosmetic and dermatological fields which is suitable for topical administration as discussed above.

These auxiliary additives may be present in the composition in a proportion from 0% to 99% (such as from 0.01% to 90%) relative to the total weight of the composition and further such as from 0.1% to 50% (if present), including all ranges and subranges therebetween.

In accordance with the present disclosure, compositions of the present disclosure can be a stand-alone product (for use by itself), or they can be a product for use in conjunction with another composition, for example it can be a basecoat (primer) composition, a color coat composition, or a topcoat (over coat) composition. It should be understood that when compositions of the present disclosure are applied to keratinous materials in the form of any of such compositions, such application can comprise one or more layers of the product. Thus, for example, application of at least one color coat composition can comprise one or more color coat layers; application of the at least topcoat composition can comprise one or more topcoat layers; and application of the at least one basecoat composition can comprise one or more basecoat layers. Preferably, such basecoat, color coat and topcoat compositions contain three or fewer layers of compositions, preferably two or fewer layers of compositions, and preferably a single layer of compositions.

During application of compositions of the present disclosure, basecoat (if present) is typically applied directly to keratinous material, color coat is typically applied either directly to the keratinous material (if no basecoat is present) or to a previously-applied basecoat, and topcoat (if present) is typically applied to a color coat.

According to preferred embodiments of the present disclosure, methods of treating, protecting, enhancing the appearance of, caring for and/or making up keratinous material by applying compositions of the present disclosure to the keratinous material in an amount sufficient to treat, enhance the appearance of, care for and/or make up the keratinous material are provided.

Preferably, "making up" keratinous material includes applying a composition comprising at least one coloring agent to the keratinous material in an amount sufficient to provide color and/or optical effect to the keratinous material.

Preferably, "protecting" keratinous material includes applying a composition of the present disclosure to protect keratinous material from damage resulting from exposure to UV rays.

In accordance with the preceding embodiments, compositions of the present disclosure are applied topically to the keratinous material in an amount sufficient to treat, enhance the appearance of, care for and/or make up the keratinous material. The compositions may be applied to the desired area as needed, preferably once or twice daily, more preferably once daily and then preferably allowed to dry before subjecting to contact such as with clothing or other objects (for example, clothes or a topcoat). Preferably, the composition is allowed to dry for about 1 minute or less, more preferably for about 45 seconds or less.

According to preferred embodiments of the present disclosure, methods of making emulsion compositions comprising combining bis-ethylhexyloxyphenol methoxyphenyl triazine, at least one lipophilic acrylic polymer, at least one $C_{12}$-$C_{24}$ fatty acid ester of a $C_2$-$C_{24}$ polyol, and at least one carboxylic or carboxylate anionic surfactant selected from the group consisting of amino acids modified with at least one $C_8$-$C_{30}$ hydrocarbon-based chain and salts thereof, during formation of the emulsion compositions are provided.

The present disclosure also envisages kits and/or prepackaged materials suitable for consumer use containing one or more compositions according to the description herein, alone or in combination with other consumer care products such as makeup products such as basecoats, topcoats, removal compositions, etc. The packaging and application device for any subject of the disclosure may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective measurements. The following examples are intended to illustrate the disclosure without limiting the scope as a result. The percentages are given on a weight basis.

Example 1—Liquid Fresh Serum SPF 50 US Tinosorb S

| Ingredient | % Concentration |
|---|---|
| WATER/AQUA | QS |
| CHELATING AGENT | 0.3 |
| PRESERVATIVE | 1 |
| POLYOL | 10 |
| WAXES/FATTY ALCOHOL/SURFACTANT | 2.5 |
| STARCH | 0.5 |
| SCLEROTIUM GUM | 0.5 |
| BUTYL METHOXYDIBENZOYLMETHANE | 3 |
| HOMOSALATE/OCTISALATE | 14 |
| BIS-ETHYLHEXYLOXYPHENOL METHOXYPHENYL TRIAZINE | 5 |
| C12-22 ALKYL ACRYLATE/ HYDROXYETHYLACRYLATE COPOLYMER | 1.5 |
| C15-19 ALKANE | 5 |
| ACTIVE AGENT | 1 |

Example 2—Liquid Fresh Serum SPF 50 US Tinosorb S (with Booster)

| INCI (US/UE) | % Concentration |
|---|---|
| WATER/AQUA | QS |
| CHELATING AGENT | 0.3 |
| PRESERVATIVE | 1 |
| POLYOL | 10 |
| WAXES/FATTY ALCOHOL/SURFACTANT | 2.5 |
| STARCH | 0.5 |
| SCLEROTIUM GUM | 0.5 |
| ETHYLHEXYL SALICYLATE | 5 |
| BUTYL METHOXYDIBENZOYLMETHANE | 3 |
| HOMOSALATE/OCTISALATE | 14 |
| ETHYLHEXYL METHOXYCRYLENE | 2 |
| BIS-ETHYLHEXYLOXYPHENOL METHOXYPHENYL TRIAZINE | 5 |
| C12-22 ALKYL ACRYLATE/ HYDROXYETHYLACRYLATE COPOLYMER | 1.5 |
| C15-19 ALKANE | 5 |
| ACTIVE AGENT | 1 |

What is claimed is:

1. An emulsion composition comprising bemotrizinol, at least one lipophilic acrylic polymer, at least one $C_{12}$-$C_{24}$ fatty acid ester of a $C_2$-$C_{24}$ polyol, and at least one carboxylic or carboxylate anionic surfactant selected from the group consisting of amino acids modified with at least one $C_8$-$C_{30}$ hydrocarbon-based chain and salts thereof, wherein the at least one lipophilic acrylic polymer comprises monomer units of formulae (A) and (B):

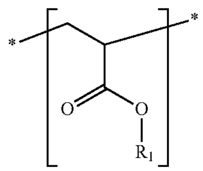
(A)

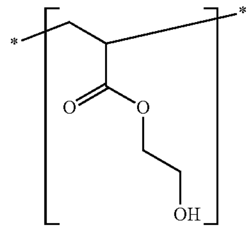
(B)

in which:

R1, independently at each instance, is chosen from alkyl and alkenyl radicals, and at least 60% by weight of the R1 groups are radicals chosen from stearyl and behenyl radicals, the percentage by weight relating to the sum of all the R1 groups present in the polymer, and the weight ratio of the sum of all the hydroxyethyl acrylate units to the sum of all the acrylate units bearing the $R_1$ group ranges from 1:30 to 1:1; and the sum of the total of units A and B is at least 95% by weight relative to the total weight of the polymer, the polymer having a number-average molecular weight Mn ranging from 2000 to 9000 g/mol; and wherein the composition has one or more of the following properties:

a critical wavelength of at least 370 nm;

a UVAPF/SPF ratio of at least 1/3; and a UVA1/UV ratio of 0.7 or higher.

2. The composition of claim 1, wherein the composition has two or more of the properties.

3. The composition of claim 1, wherein the composition also has an SPF value of at least 30.

4. The composition of claim 1, wherein the at least one lipophilic acrylic polymer comprises at least 70% by weight of R1 groups which are chosen from stearyl and behenyl radicals.

5. The composition of claim 1, wherein the at least one lipophilic acrylic polymer comprises all R1 groups which are radicals chosen from stearyl and behenyl radicals.

6. The composition of claim 1, wherein the pH is 6 or greater.

7. The composition of claim 1, wherein the composition is free of mineral UV filters.

8. The composition of claim 1, wherein the composition comprises 10% or less by weight relative to the total weight of composition of additional organic UV filters.

9. The composition of claim 1, wherein the composition is free of oxybenzone and/or octinoxate.

10. The composition of claim 1, further comprising at least one coloring agent.

11. The composition of claim 1, further comprising at least one active principle.

12. The composition of claim 1, wherein the composition has all three of the properties.

13. The composition of claim 2, wherein the composition also has an SPF value of at least 30.

14. The composition of claim 12, wherein the composition also has an SPF value of at least 30.

15. The composition of claim 1, wherein the composition is a serum.

16. The composition of claim 1, further comprising at least one vitamin.

* * * * *